US009176847B2

(12) United States Patent
Malinowski et al.

(10) Patent No.: US 9,176,847 B2
(45) Date of Patent: Nov. 3, 2015

(54) MANAGING DIAGNOSTIC INFORMATION (71) Applicant: International Business Machines Corporation, Armonk, NY (US)

(72) Inventors: Joseph V. Malinowski, Bridgeview, IL (US); Miguel A. Perez, Tucson, AZ (US); David C. Reed, Tucson, AZ (US); Max D. Smith, Tucson, AZ (US)

(73) Assignee: International Business Machines Corporation, Armonk, NY (US)

( * ) Notice: Subject to any disclaimer, the term of this patent is extended or adjusted under 35 U.S.C. 154(b) by 196 days.

(21) Appl. No.: 13/899,712

(22) Filed: May 22, 2013

(65) Prior Publication Data

US 2014/0351655 A1 Nov. 27, 2014

(51) Int. Cl.
*G06F 11/36* (2006.01)
*G06F 11/07* (2006.01)
*G06F 11/34* (2006.01)

(52) U.S. Cl.
CPC ........ *G06F 11/3636* (2013.01); *G06F 11/0778* (2013.01); *G06F 11/3466* (2013.01)

(58) Field of Classification Search
CPC .......................... G06F 11/3466; G06F 11/3636
See application file for complete search history.

(56) References Cited

U.S. PATENT DOCUMENTS

| | | | | | |
|---|---|---|---|---|---|
| 4,103,329 | A | * | 7/1978 | Davis et al. | 712/300 |
| 5,584,039 | A | * | 12/1996 | Johnson et al. | 710/6 |
| 5,619,644 | A | * | 4/1997 | Crockett et al. | 714/45 |
| 5,717,956 | A | * | 2/1998 | Shinosaka et al. | 710/65 |
| 5,896,538 | A | * | 4/1999 | Blandy et al. | 717/127 |
| 6,745,351 | B1 | * | 6/2004 | Mastro | 714/57 |
| 6,864,993 | B1 | * | 3/2005 | Roberts et al. | 358/1.9 |
| 7,698,604 | B2 | | 4/2010 | Bartlett et al. | |
| 8,250,243 | B2 | | 8/2012 | Berger et al. | |
| 8,327,193 | B2 | | 12/2012 | Enarson et al. | |
| 2005/0182750 | A1 | * | 8/2005 | Krishna et al. | 707/1 |
| 2008/0126301 | A1 | * | 5/2008 | Bank et al. | 707/3 |
| 2008/0155349 | A1 | * | 6/2008 | Ivanov et al. | 714/45 |
| 2009/0012748 | A1 | * | 1/2009 | Beish et al. | 702/187 |
| 2009/0106741 | A1 | * | 4/2009 | Dageville et al. | 717/128 |
| 2009/0132863 | A1 | * | 5/2009 | Ashfield et al. | 714/45 |
| 2009/0183034 | A1 | * | 7/2009 | Houlihane et al. | 714/45 |
| 2009/0228431 | A1 | * | 9/2009 | Dunagan et al. | 707/2 |
| 2010/0107143 | A1 | * | 4/2010 | Emberling | 717/128 |
| 2010/0185903 | A1 | | 7/2010 | Horn et al. | |
| 2010/0257510 | A1 | * | 10/2010 | Horley et al. | 717/128 |
| 2011/0035724 | A1 | * | 2/2011 | Kettley et al. | 717/106 |
| 2011/0161742 | A1 | * | 6/2011 | Bird et al. | 714/47.2 |

(Continued)

OTHER PUBLICATIONS

IBM, "Comprehensive "Drive" Diagnostics in Automation Environments", IP.com Prior Art Database Technical Disclosure, published Apr. 29, 2005. IP.com No. IPCOM000124607D.

*Primary Examiner* — Joshua P Lottich (74) *Attorney, Agent, or Firm* — Richard A. Wilhelm; Robert Sullivan (57) ABSTRACT

A method of and system for managing diagnostic information is disclosed. The method and system may include creating a data space in volatile memory. The data space may be configured to collect a selected diagnostic information. The selected diagnostic information may include a first diagnostic information from a first source and a second diagnostic information from a second source. The method and system may include collecting in the data space the selected diagnostic information. The method and system may include releasing from the data space at least a portion of the selected diagnostic information in response to a triggering event.

20 Claims, 4 Drawing Sheets

(56) References Cited

U.S. PATENT DOCUMENTS

| | | |
|---|---|---|
| 2011/0167302 A1 | 7/2011 | McCune et al. |
| 2012/0144236 A1 | 6/2012 | Black et al. |
| 2012/0159248 A1 | 6/2012 | Inamdar et al. |
| 2013/0019128 A1 | 1/2013 | Yamasaki et al. |
| 2013/0055032 A1* | 2/2013 | Cole et al. ............. 714/45 |
| 2014/0019985 A1* | 1/2014 | Krajec ............. 718/102 |
| 2014/0025572 A1* | 1/2014 | Krajec ............. 705/40 |

* cited by examiner

Begin
301

↓

Creating a data space in volatile memory configured to collect a selected diagnostic information, the selected diagnostic information including a first diagnostic information from a first source and a second diagnostic information from a second source

310

↓

Collecting in the data space the selected diagnostic information

320

↓

Releasing from the data space at least a portion of the selected diagnostic information in response to a triggering event

330

↓

Done
399

FIG. 3

FIG. 4

MANAGING DIAGNOSTIC INFORMATION

TECHNICAL FIELD

This disclosure relates generally to monitoring computer systems and, more particularly, relates to diagnostic information.

BACKGROUND

Diagnostic information associated with an error event may be gathered. The diagnostic information may be utilized in an attempt to determine a cause of the error event. For example, a user may examine diagnostic information such as system records for data related to the error event. Error events may lead to integrity problems, application outages, or expend resources. As such, significant costs may be associated with error events.

SUMMARY

Aspects of the disclosure may include a method of and system for managing diagnostic information. The method and system may include creating a data space in volatile memory. The data space may be configured to collect a selected diagnostic information. The selected diagnostic information may include a first diagnostic information from a first source and a second diagnostic information from a second source. The method and system may include collecting in the data space the selected diagnostic information. The method and system may include releasing from the data space at least a portion of the selected diagnostic information in response to a triggering event.

Aspects of the disclosure may include the selected diagnostic information being a subset of an all-inclusive diagnostic information of the first and second sources. The selected diagnostic information may include an intermixing of the first diagnostic information and the second diagnostic information. The triggering event may include an error event. Releasing from the data space at least a portion of the selected diagnostic information may include dumping from the data space at least a portion of the selected diagnostic information. The triggering event may include a collection threshold event. Releasing from the data space at least a portion of the selected diagnostic information may include wrapping in the data space at least a portion of the selected diagnostic information. Aspects of the disclosure may collect in the memory diagnostic information for time periods before, during, and after error events. Aspects of the disclosure may be beneficial to reducing costs associated with error events.

DETAILED DESCRIPTION

Computer systems may be monitored and performance may be analyzed. Diagnostic information may exist that is associated with an error event. The diagnostic information may be gathered. The diagnostic information may be utilized in an attempt to determine a cause of the error event. The cause of the error event may be avoided in future cases. Costs associated with error events may be reduced.

It may be challenging to gather diagnostic information for error events. The diagnostic information may be desired to be gathered from multiple sources. The diagnostic information may be captured at varying times. Saving the diagnostic information to disk may expend resources. If the error events occur infrequently or unpredictably, capturing documentation may be particularly challenging. Users do not want to experience error events, and certainly do not want to experience error events multiple times just to gather documentation. Capturing the desired documentation from multiple sources in case of an error event may be beneficial to reducing costs associated with error events.

Aspects of the disclosure may include managing diagnostic information. A data space may be created. The data space may be created in a memory (e.g., volatile memory). The memory may be configured to collect a selected diagnostic information. The selected diagnostic information may include a first diagnostic information from a first source. The selected diagnostic information may include a second diagnostic information from a second source. The selected diagnostic information may be collected in the data space.

Aspects of the disclosure may include releasing from the data space at least a portion of the selected diagnostic information. Such release may occur in response to a triggering event. The triggering event may include an error event. Releasing from the data space at least a portion of the selected diagnostic information may include dumping from the data space at least a portion of the selected diagnostic information. The triggering event may include a collection threshold event. Releasing from the data space at least a portion of the selected diagnostic information may include wrapping in the data space at least a portion of the selected diagnostic information.

Aspects of the disclosure may include the selected diagnostic information being a subset of an all-inclusive diagnostic information of the first and second sources. The selected diagnostic information may include an intermixing of the first diagnostic information and the second diagnostic information. The selected diagnostic information may include at least one of error information, data from a data set, metadata about a data set, system data, application history, performance information, and input-output (I/O) tracing. In particular, the selected diagnostic information may include a channel command or a supervisor call (SVC). Aspects of the disclosure may collect in the memory diagnostic information for time periods before, during, and after error events. Aspects of the disclosure may be beneficial to reducing costs associated with error events.

Figure 1:
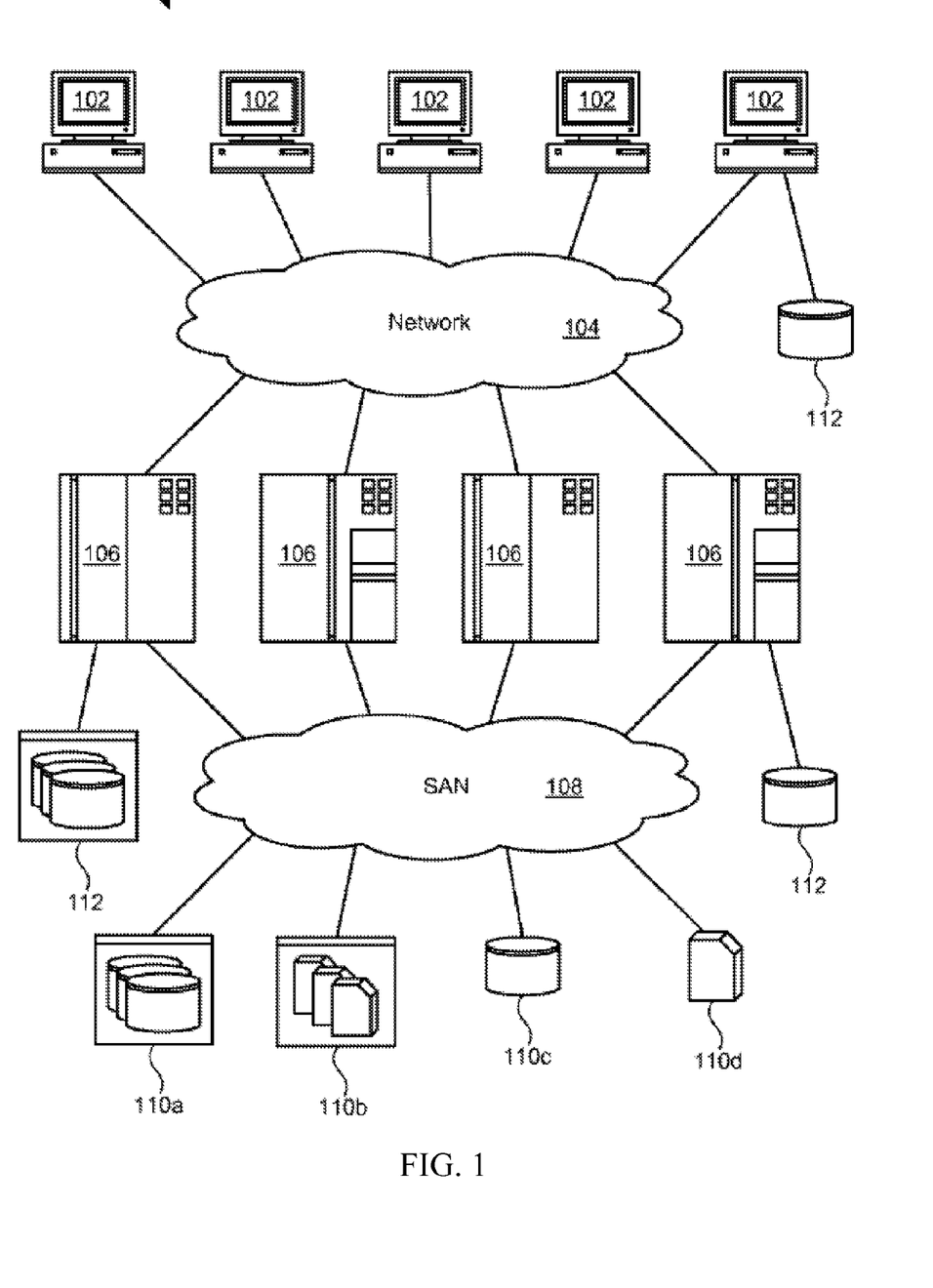
FIG. 1 illustrates an example network architecture according to an embodiment.

FIG. 1 illustrates an example network architecture 100 according to an embodiment. The network architecture 100 is presented to show one example of an environment where a system and method in accordance with the disclosure may be implemented. The network architecture 100 is presented only by way of example and is not intended to be limiting. The system and methods disclosed herein may be applicable to a wide variety of different computers, servers, storage devices, and network architectures, in addition to the network architecture 100 shown.

As shown, the network architecture 100 includes one or more computers 102, 106 interconnected by a network 104. The network 104 may include, for example, a local-area-network (LAN), a wide-area-network (WAN), the Internet, an intranet, or the like. In certain embodiments, the computers 102, 106 may include both client computers 102 and server computers 106 (also referred to herein as "host systems" 106). In general, client computers 102 may initiate communication sessions, whereas server computers 106 may wait for requests from the client computers 102. In certain embodiments, the computers 102 and/or servers 106 may connect to one or more internal or external direct-attached storage systems 112 (e.g., arrays of hard-disk drives, solid-state drives, tape drives, etc.). These computers 102, 106 and direct-attached storage systems 112 may communicate using protocols such as ATA, SATA, SCSI, SAS, Fibre Channel, or the like. One or more of the storage systems 112 may contain storage pools that may benefit from management techniques of the disclosure.

The network architecture 100 may, in certain embodiments, include a storage network 108 behind the servers 106, such as a storage-area-network (SAN) or a LAN (e.g., when using network-attached storage). This network 108 may connect the servers 106 to one or more storage systems 110, such as arrays 110a of hard-disk drives or solid-state drives, tape libraries 110b, individual hard-disk drives 110c or solid-state drives 110c, tape drives 110d, CD-ROM libraries, or the like. To access a storage system 110, a host system 106 may communicate over physical connections from one or more ports on the host 106 to one or more ports on the storage system 110. A connection may be through a switch, fabric, direct connection, or the like. In certain embodiments, the servers 106 and storage systems 110 may communicate using a networking standard such as Fibre Channel (FC). One or more of the storage systems 110 may contain storage pools that may benefit from management techniques according to the disclosure.

Figure 2:
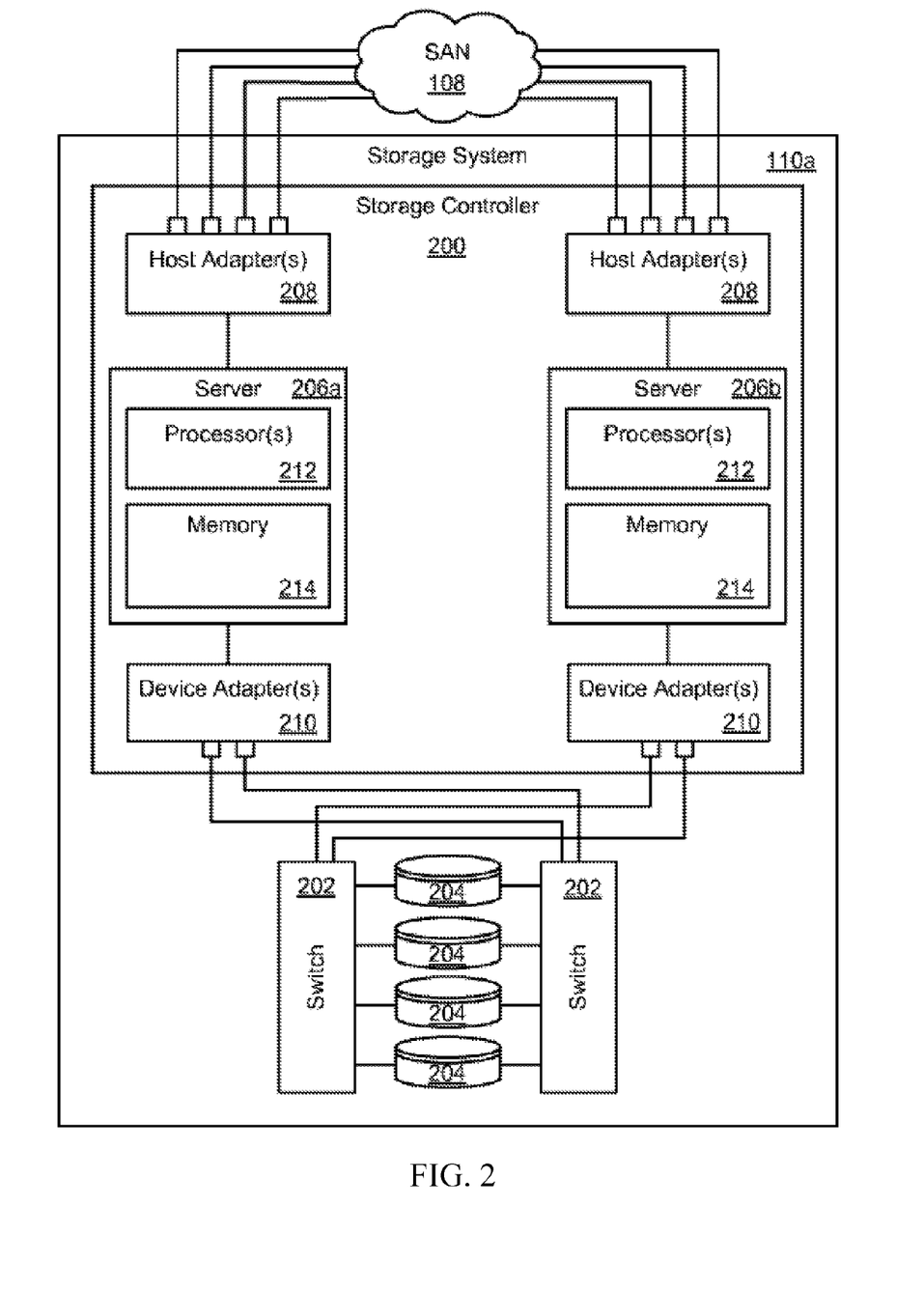
FIG. 2 illustrates an example storage system containing an array of storage devices according to an embodiment.

FIG. 2 illustrates an example storage system 110a containing an array of storage devices 204 (e.g., hard-disk drives and/or solid-state drives) according to an embodiment. The internal components of the storage system 110a are shown in accordance with the disclosure and may be used to manage diagnostic information associated with such a storage system 110a. Nevertheless, management techniques according to the disclosure may also be implemented within other storage systems 110, 112. As shown, the storage system 110a includes a storage controller 200, one or more switches 202, and one or more storage devices 204, such as hard-disk drives or solid-state drives (e.g., flash-memory-based drives). The storage controller 200 may enable one or more hosts 106 (e.g., open system and/or mainframe servers 106) to access data stored in the one or more storage devices 204.

As shown in FIG. 2, the storage controller 200 includes one or more servers 206. The storage controller 200 may also include host adapters 208 and device adapters 210 to connect the storage controller 200 to host devices 106 and storage devices 204, respectively. Multiple servers 206a, 206b may provide redundancy to ensure that data is always available to connected hosts 106. Thus, when one server 206a fails, the other server 206b may remain functional to ensure that I/O is able to continue between the hosts 106 and the storage devices 204. This process may be referred to as a "failover."

Particular enterprise storage systems may have a storage system 110a having an architecture similar to that illustrated in FIG. 2. Particular enterprise storage systems may include a high-performance, high-capacity storage controller providing disk storage that is designed to support continuous operations. Particular enterprise storage systems may use servers 206a, 206b, which may be integrated with a virtualization engine technology. Nevertheless, management techniques according to the disclosure are not limited to any specific enterprise storage system 110a, but may be implemented in any comparable or analogous storage system 110 regardless of the manufacturer, product name, or components or component names associated with the storage system 110. Any storage system 110 that could benefit from management techniques according to the disclosure is deemed to fall within the scope of the disclosure. Thus, the enterprise storage system shown is presented only by way of example and is not intended to be limiting.

In selected embodiments, each server 206 includes one or more processors 212 (e.g., n-way symmetric multiprocessors) and memory 214. The memory 214 may include volatile memory (e.g., RAM) as well as non-volatile memory (e.g., ROM, EPROM, EEPROM, hard disks, flash memory, etc.). The volatile memory and non-volatile memory may store software modules that run on the processor(s) 212 and are used to access data in the storage devices 204. The servers 206 may host at least one instance of these software modules. These software modules may manage all read and write requests to logical volumes in the storage devices 204.

Figure 3:
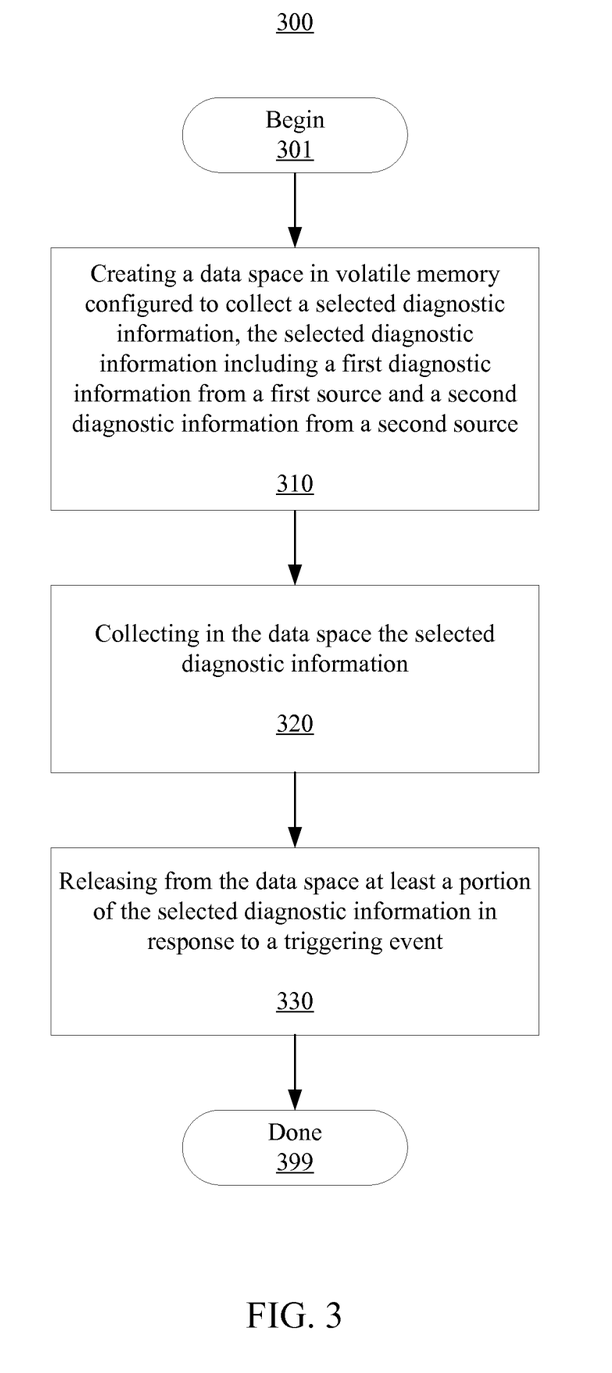
FIG. 3 is a flowchart illustrating an operation for managing diagnostic information according to an embodiment.

FIG. 3 is a flowchart illustrating an operation 300 for managing diagnostic information according to an embodiment. Diagnostic information may include data related to error events. Operation 300 may be beneficial to reducing costs associated with error events. Operation 300 may begin at block 301. A data space may be created (e.g., established) at block 310. In embodiments, the data space may be considered to be at least one of centralized, collective, combined, common, community, gathered, merged, pooled, and shared. The data space may be created in a memory (e.g., volatile memory). The memory may be configured to collect selected diagnostic information.

The selected diagnostic information may include a first diagnostic information from a first source. The selected diagnostic information may include a second diagnostic information from a second source. In embodiments, the first and second sources may include at least one of an application, a component, a job, a program, a task, and a user activity. The selected diagnostic information may be collected in the data space at block 320.

In embodiments, the selected diagnostic information may include an intermixing of the first diagnostic information and the second diagnostic information. Intermixing may include data of the sources being merged, for example, by timestamps and related functions. Therefore, for instance, processes occurring together, at substantially the same time, or in a time window preceding error events may be analyzed. For example, a cause of a resource contention error (e.g., error due to a conflict over access to a shared resource) may be more apparent or more quickly diagnosed with the first and second diagnostic information in the data space which is shared by multiple sources and may include intermixed data. In such example, the data is not spread over multiple disks but is instead in the memory. Also in such example, the intermixed data may clarify the nature of the conflict between resources.

In embodiments, the selected diagnostic information may be a subset of an all-inclusive diagnostic information of the first and second sources. The subset may include the selected diagnostic information consisting of diagnostic elements smaller in quantity or quality than the all-inclusive diagnostic information. The all-inclusive diagnostic information may include all diagnostic information (e.g., all data related to error events) of both the first source and the second source. The subset of the all-inclusive diagnostic information may include data vital, essential, or merely helpful to understanding events related to the first and second sources.

In embodiments, the selected diagnostic information may include, for example, at least one of error information, data from a data set, metadata about a data set, system data, application history, performance information, and input-output (I/O) tracing. For instance, performance information may include resource contention. In particular embodiments, the selected diagnostic information may include a channel command. The channel command may be a word instructing an action. The channel command may be related to (e.g., recorded by) a generalized trace facility (GTF). In particular embodiments, the selected diagnostic information may include a supervisor call (SVC). The SVC may include a processor instruction directing the processor to pass control of a computer to a supervisor program of an operating system. The SVC may include a request for a specific operating system service from an application program or part of the operating system. The selected diagnostic information may include at least one of clear subchannel operations, external interruptions, halt subchannel operations, I/O interruptions, program-controlled interruptions, non-program-controlled interruptions, end of sense interruptions, modify subchannel operations, recovery routines, start subchannel operations, resume channel operations, and SVC interruptions.

Operation 300 may collect in the memory diagnostic information for time periods before, during, and after error events. In embodiments, collecting may include at least one of capturing, confining, corralling, detaining, gathering, holding, preserving, receiving, retaining, seizing, storing, and writing. The collecting may be a short-term storing. The collecting may be an ongoing capturing. The collecting may be a continual writing. A variety of combinations of the collecting are contemplated (e.g., ongoing capturing, continual gathering).

At least a portion of the selected diagnostic information may be released from the data space at block 330. Such release may occur in response to a triggering event. The triggering event may include an error event. In embodiments, the error event may include an actual error (e.g., access to resource improperly locked) or a perceived error (e.g., access to resource exceeding a temporal latency threshold). For example, the error event may include at least one of an error occurring, detecting an error, detecting a potential error, and a potential error occurring. The triggering event may include a collection threshold event. In embodiments, the collection threshold event may include reaching a collection threshold value. The collection threshold value may be an amount of data space or memory allocated to collect the selected diagnostic information. For example, the collection threshold value may be reached when the data space runs out of room to collect further data. The data space may run out of room to collect further data after, for instance, five seconds or one-hundred kilobytes of collection.

In embodiments, releasing may include at least one of copying, deleting, dumping, erasing, reading, recording, saving, and wrapping. Releasing may or may not clear the data space. In embodiments, releasing from the data space at least a portion of the selected diagnostic information may include dumping from the data space at least a portion of the selected diagnostic information. Dumping may include saving off in a different data space. Dumping may include recording data elsewhere (e.g., disk, nonvolatile memory) for use in subsequent problem analysis.

In embodiments, releasing from the data space at least a portion of the selected diagnostic information may include wrapping in the data space at least a portion of the selected diagnostic information. Wrapping may include selectively overwriting. Selectively overwriting may include writing over a first portion of the selected diagnostic information deemed to be a lower priority than a second portion of the selected diagnostic information. The first portion of the selected diagnostic information in such case may no longer exist subsequent to the overwriting. Wrapping may occur in a first-in-first-out (FIFO) order.

Operation 300 may conclude at block 399. Operation 300 may provide historical data (and data from related sources) leading up to error events. Multiple sources may be able to record information associated with error events to a common data space. Operation 300 may gather information related to error events. Related information may be grouped together in the common data space. Operation 300 may be beneficial to reducing costs associated with error events.

For example, when an I/O error takes place, I/O drivers may record a subset of selected diagnostic information that may be recorded in a typical GTF trace. Selected diagnostic information may be written to memory rather than disk, and a smaller amount of data may be recorded, which may decrease performance impact. When the collection threshold event occurs, trace entries may wrap. When the error event occurs, dumping or saving off in a different data space may occur. For a non-retryable event, the data may be dumped to disk. For a retryable error, the data may be copied to a different data space where it is held until the retry events reach a retry threshold value or the I/O succeeds. If the retry is successful, the data may be discarded or dumped, depending on a user setting. If the retryable error continues to fail, both the original error and the retried error may be dumped. In addition, when an abnormal end occurs in a primary data space of the source, the associated selected diagnostic information in the data space may be dumped. As another example, when an SVC is made and a job abnormally ends, the data space may include an SVC history of SVCs issued leading up to the time of the failure. Other possibilities are considered.

Figure 4:
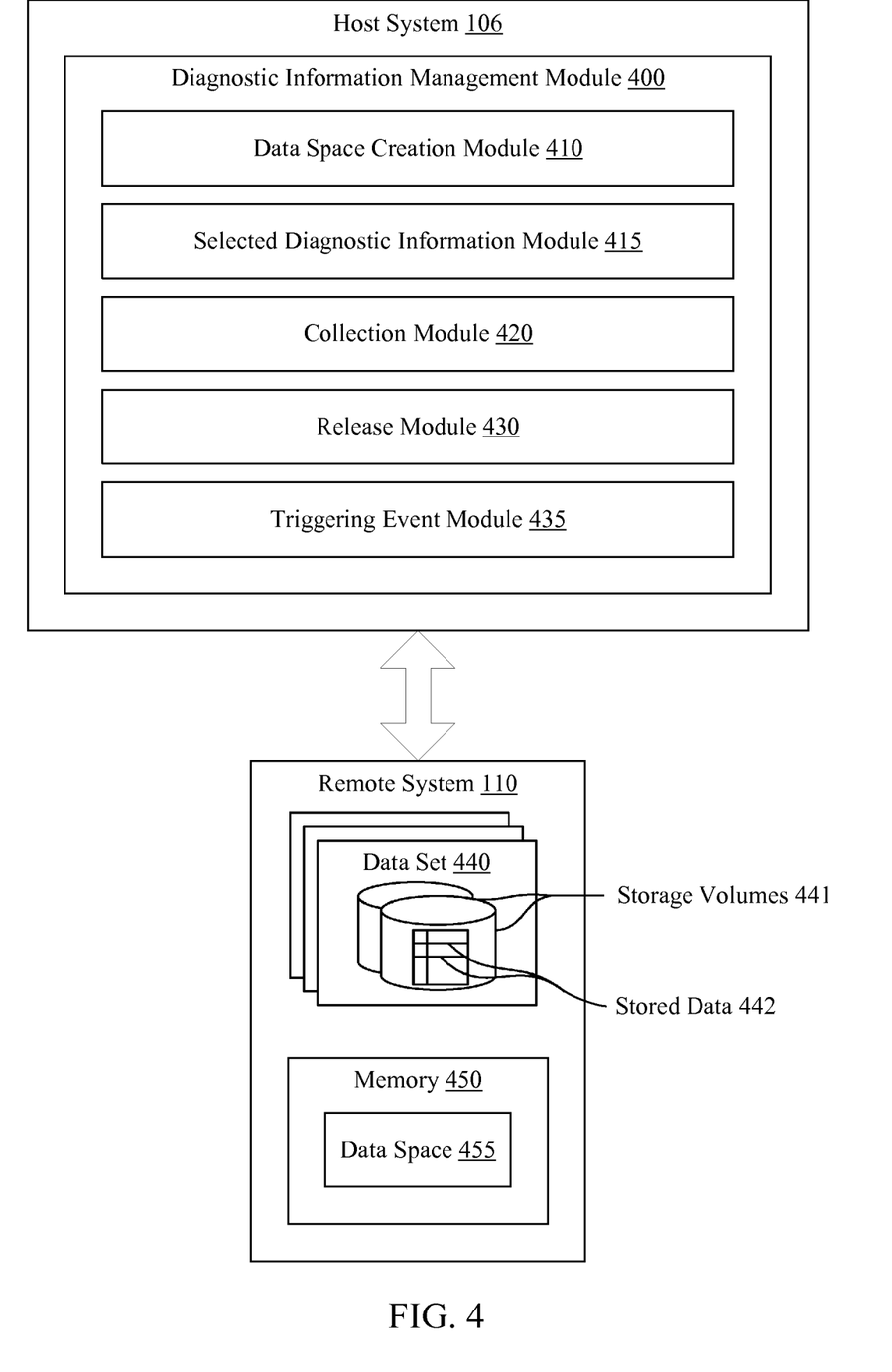
FIG. 4 shows modules of a system implementing an operation according to an embodiment.

FIG. 4 shows modules of a system implementing operation 300 according to an embodiment. In embodiments, operation 300 may be implemented in the form of one or more modules. These modules may be implemented in hardware, software or firmware executable on hardware, or a combination thereof. For example, module functionality that may occur in a host system 106 may actually be implemented in a remote system 110 and vice versa. Other functionality may be distributed across the host system 106 and the remote system 110.

A host system 106 may include a diagnostic information management module 400. The diagnostic information management module 400 may manage diagnostic information. The diagnostic information management module 400 may include a data space creation module 410, a selected diagnostic information module 415, a collection module 420, a release module 430, and a triggering event module 435. The remote system 110 may have a data set 440 comprising storage volumes 441 adapted to have storage data 442. The remote system 110 may have a memory 450. The memory 450 may be volatile memory. The memory 450 may include a data space 455. In embodiments, the data space 455 may be considered to be at least one of centralized, collective, combined, common, community, gathered, merged, pooled, and shared.

The data space creation module 410 may create (e.g., establish) the data space 455 in the memory 450 in an embodiment. The memory 450 may be configured to collect a selected diagnostic information. The selected diagnostic information module 415 may have the selected diagnostic information including a first diagnostic information from a first source and a second diagnostic information from a second source. In embodiments, the first and second sources may include at least one of an application, a component, a job, a program, a task, and a user activity. The selected diagnostic information and embodiments thereof may be similar or the same as described above relating to FIG. 3.

The collection module 420 may collect in the data space 455 the selected diagnostic information. The collection module 420 may collect in the memory diagnostic information for time periods before, during, and after error events. In embodiments, collecting may include at least one of capturing, confining, corralling, detaining, gathering, holding, preserving, receiving, retaining, seizing, storing, and writing. The collecting may be a short-term storing. The collecting may be an ongoing capturing. The collecting may be a continual writing. A variety of combinations of the collecting are contemplated (e.g., ongoing capturing, continual gathering).

The release module 430 may release from the data space 455 at least a portion of the selected diagnostic information in response to a triggering event. Such release may occur in response to a triggering event. The triggering event module 435 may characterize the triggering event. The triggering event may include an error event. In embodiments, the error event may include an actual error (e.g., access to resource improperly locked) or a perceived error (e.g., access to resource exceeding a temporal latency threshold). For example, the error event may include at least one of an error occurring, detecting an error, detecting a potential error, and a potential error occurring. The triggering event may include a collection threshold event. In embodiments, the collection threshold event may include reaching a collection threshold value. The collection threshold value may be an amount of data space or memory allocated to collect the selected diagnostic information. For example, the collection threshold value may be reached when the data space runs out of room to collect further data.

In embodiments, releasing performed by the release module 430 may include at least one of copying, deleting, dumping, erasing, reading, recording, saving, and wrapping. Releasing may or may not clear the data space 455. In embodiments, releasing from the data space 455 at least a portion of the selected diagnostic information may include dumping from the data space at least a portion of the selected diagnostic information. Dumping may include saving off in a different data space. Dumping may include recording data elsewhere (e.g., disk, nonvolatile memory) for use in subsequent problem analysis.

In embodiments, releasing from the data space 455 at least a portion of the selected diagnostic information may include wrapping in the data space 455 at least a portion of the selected diagnostic information. Wrapping may include selectively overwriting. Selectively overwriting may include writing over a first portion of the selected diagnostic information deemed to be a lower priority than a second portion of the selected diagnostic information. The first portion of the selected diagnostic information in such case may no longer exist subsequent to the overwriting. Wrapping may occur in a first-in-first-out (FIFO) order.

The diagnostic information management module 400 may provide historical data (and data from related sources) leading up to error events. Multiple sources may be able to record information associated with error events to the data space 455. The diagnostic information management module 400 may gather information related to error events. Related information may be grouped together in the data space 455. The diagnostic information management module 400 may be beneficial to reducing costs associated with error events.

In addition to embodiments described above, other embodiments having fewer operational steps, more operational steps, or different operational steps are contemplated. Also, some embodiments may perform some or all of the above operational steps in a different order. The modules are listed illustratively according to an embodiment and are not meant to indicate necessity of a particular module or exclusivity of other potential modules.

In the foregoing, reference is made to various embodiments. It should be understood, however, that this disclosure is not limited to the specifically described embodiments. Instead, any combination of the described features and elements, whether related to different embodiments or not, is contemplated to implement and practice this disclosure. Many modifications and variations may be apparent to those of ordinary skill in the art without departing from the scope and spirit of the described embodiments. Furthermore, although embodiments of this disclosure may achieve advantages over other possible solutions or over the prior art, whether or not a particular advantage is achieved by a given embodiment is not limiting of this disclosure. Thus, the described aspects, features, embodiments, and advantages are merely illustrative and are not considered elements or limitations of the appended claims except where explicitly recited in a claim(s).

As will be appreciated by one skilled in the art, aspects of the present disclosure may be embodied as a system, method, or computer program product. Accordingly, aspects of the present disclosure may take the form of an entirely hardware embodiment, an entirely software embodiment (including firmware, resident software, micro-code, etc.), or an embodiment combining software and hardware aspects that may all generally be referred to herein as a "circuit," "module," or "system." Furthermore, aspects of the present disclosure may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination thereof. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination thereof. In the context of this disclosure, a computer readable storage medium may be any tangible medium that can contain, or store, a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wire line, optical fiber cable, RF, etc., or any suitable combination thereof.

Computer program code for carrying out operations for aspects of the present disclosure may be written in any combination of one or more programming languages, including: an object oriented programming language such as Java, Smalltalk, C++, or the like; and conventional procedural programming languages, such as the "C" programming language or similar programming languages. The program code may execute as specifically described herein. In addition, the program code may execute entirely on the user's computer, partly on the user's computer, as a stand-alone software package, partly on the user's computer and partly on a remote computer, or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present disclosure have been described with reference to flowchart illustrations, block diagrams, or both, of methods, apparatuses (systems), and computer program products according to embodiments of this disclosure. It will be understood that each block of the flowchart illustrations or block diagrams, and combinations of blocks in the flowchart illustrations or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions or acts specified in the flowchart or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function or act specified in the flowchart or block diagram block or blocks.

The computer program instructions may also be loaded onto a computer, other programmable data processing apparatus, or other devices to cause a series of operational steps to be performed on the computer, other programmable apparatus, or other devices to produce a computer implemented process such that the instructions which execute on the computer or other programmable apparatus provide processes for implementing the functions or acts specified in the flowchart or block diagram block or blocks.

Embodiments according to this disclosure may be provided to end-users through a cloud-computing infrastructure. Cloud computing generally refers to the provision of scalable computing resources as a service over a network. More formally, cloud computing may be defined as a computing capability that provides an abstraction between the computing resource and its underlying technical architecture (e.g., servers, storage, networks), enabling convenient, on-demand network access to a shared pool of configurable computing resources that can be rapidly provisioned and released with minimal management effort or service provider interaction. Thus, cloud computing allows a user to access virtual computing resources (e.g., storage, data, applications, and even complete virtualized computing systems) in "the cloud," without regard for the underlying physical systems (or locations of those systems) used to provide the computing resources.

Typically, cloud-computing resources are provided to a user on a pay-per-use basis, where users are charged only for the computing resources actually used (e.g., an amount of storage space used by a user or a number of virtualized systems instantiated by the user). A user can access any of the resources that reside in the cloud at any time, and from anywhere across the Internet. In context of the present disclosure, a user may access applications or related data available in the cloud. For example, the nodes used to create a stream computing application may be virtual machines hosted by a cloud service provider. Doing so allows a user to access this information from any computing system attached to a network connected to the cloud (e.g., the Internet).

The flowchart and block diagrams in the figures illustrate the architecture, functionality, and operation of possible implementations of systems, methods, and computer program products according to various embodiments of the present disclosure. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams or flowchart illustration, and combinations of blocks in the block diagrams or flowchart illustration, can be implemented by special purpose hardware-based systems that perform the specified functions or acts, or combinations of special purpose hardware and computer instructions.

While the foregoing is directed to exemplary embodiments, other and further embodiments of the disclosure may be devised without departing from the basic scope thereof, and the scope thereof is determined by the claims that follow.

What is claimed is:

1. A computer-implemented method for managing diagnostic information, the method comprising:
   allocating a data space in a volatile memory to store a selected diagnostic information, the selected diagnostic information including a first diagnostic information from a first source and a second diagnostic information from a second source, the selected diagnostic information being a subset of information recorded by a generalized trace facility recording events of the first and second sources;
   collecting in the data space the selected diagnostic information, the collecting including:
      an intermixing of the first diagnostic information and the second diagnostic information during a time window preceding an error event, and
      a wrapping in the data space of at least a portion of the selected diagnostic information when a collection threshold amount of the data space is reached; and
   dumping from the data space to a non-volatile memory at least a portion of the selected diagnostic information in response to the error event.

2. The method of claim 1, wherein the first source is an application program and the second source is an input/output component.

3. The method of claim 1, wherein the selected diagnostic information includes a third source and a fourth source, and the first source is a first server, the second source is a second server, the third source is a host adapter, and the fourth source is a device adapter.

4. The method of claim 1, wherein the error event includes an improper lock-of a resource.

5. The method of claim 1, wherein the error event includes an attempt to access a resource exceeding a latency threshold.

6. The method of claim 1, wherein the selected diagnostic information includes a first interrupt by the first source and a second interrupt by the second source.

7. The method of claim 1, wherein the selected diagnostic information includes a first application history of the first source and a second application history of the second source.

8. The method of claim 1, wherein the selected diagnostic information includes a first channel command by the first source and a second channel command by the second source.

9. The method of claim 1, wherein the selected diagnostic information includes a first supervisor call (SVC) by the first source and a second SVC by the second source.

10. A system for managing diagnostic information, comprising:
a remote system; and
a host system, at least one of the remote system and the host system including a diagnostic information management module, the diagnostic information management module comprising:
a data space creation module to allocate a data space in volatile memory configured to store a selected diagnostic information, the selected diagnostic information including a first diagnostic information from a first source and a second diagnostic information from a second source, the selected diagnostic information being a subset of information recorded by a generalized trace facility recording events of the first and second sources;
a collection module to receive in the data space the selected diagnostic information, intermix the first and second diagnostic information during a time window preceding an error event, and release at least a portion of the selected diagnostic information when a collection threshold amount of the data space is reached; and
a release module to dump from the data space to a non-volatile memory at least a portion of the selected diagnostic information in response to the error event.

11. The method of claim 10, wherein the first source is an application program and the second source is an input/output component.

12. The system of claim 10, wherein the selected diagnostic information includes a third source and a fourth source, and the first source is a first server, the second source is a second server, the third source is a host adapter, and the fourth source is a device adapter.

13. The system of claim 10, wherein the error event includes an improper lock of a resource.

14. The system of claim 10, wherein the error event includes an attempt to access a resource exceeding a latency threshold.

15. The system of claim 10, wherein the selected diagnostic information includes a first interrupt by the first source and a second interrupt by the second source.

16. The system of claim 10, wherein the selected diagnostic information includes a first input-output (I/O) tracing of the first source and a second I/O tracing of the second source.

17. The system of claim 10, wherein the selected diagnostic information includes a first channel command by the first source and a second channel command by the second source channel command.

18. The system of claim 10, wherein the selected diagnostic information includes a first supervisor call (SVC) by the first source and a second SVC by the second source supervisor call (SVC).

19. A storage system, comprising:
a remote system having two or more storage devices; and
a storage controller having a diagnostic information management module, the diagnostic information management module comprising:
a data space creation module to allocate a data space in volatile memory configured to store a selected diagnostic information, the selected diagnostic information including a diagnostic information from a plurality of sources, the selected diagnostic information being a subset of information recorded by a generalized trace facility recording events of the plurality of sources;
a collection module to receive in the data space the selected diagnostic information, the selected diagnostic information including a first portion and a second portion, wherein the collection module is configured to selectively overwrite the first portion when a collection threshold amount of the data space is reached, the first portion having a lower priority than the second portion; and
a release module to dump from the data space to a non-volatile memory at least a portion of the selected diagnostic information in response to an error event.

20. The storage system of claim 19, wherein the plurality of sources includes a first source, a second source, a third source, and a fourth source, and the first source is a first server, the second source is a second server, the third source is a host adapter, and the fourth source is a device adapter.

* * * * *